(12) United States Patent
Tewari et al.

(10) Patent No.: US 10,730,869 B2
(45) Date of Patent: Aug. 4, 2020

(54) **PROCESS FOR EXTRACTING ALPHA YOHIMBINE (RAUWOLSCINE) FROM *RAUWOLFIA* SPECIES**

(71) Applicant: Pawan Kumar Goel, Haryana (IN)

(72) Inventors: Kiran Tewari, Haryana (IN); Ashok Sharma, Haryana (IN)

(73) Assignee: Pawan Kumar Goel, Panchkula (IN)

( * ) Notice: Subject to any disclaimer, the term of this patent is extended or adjusted under 35 U.S.C. 154(b) by 0 days.

(21) Appl. No.: 16/406,422

(22) Filed: May 8, 2019

(65) Prior Publication Data

US 2019/0330203 A1 Oct. 31, 2019

Related U.S. Application Data

(63) Continuation of application No. PCT/IN2017/050518, filed on Nov. 9, 2017.

(30) Foreign Application Priority Data

Nov. 9, 2016 (IN) .............................. 201611038337

(51) Int. Cl.
*C07D 459/00* (2006.01)
*A61K 36/24* (2006.01)
*B01D 11/02* (2006.01)

(52) U.S. Cl.
CPC ........ *C07D 459/00* (2013.01); *B01D 11/0288* (2013.01)

(58) Field of Classification Search
CPC ... C07D 459/00; B01D 11/0288; A61K 36/24
See application file for complete search history.

(56) References Cited

PUBLICATIONS

ABCAM Product Datasheet (p. 1-2; downloaded https://www.abcam.com/rauwolscine-hydrochloride-alpha2-adrenergic-antagonist-ab120875.html#top-0 on Nov. 1, 2019.*
ABCAM Safety Datasheet (p. 1-6, Revision Date Jul. 13, 2015).*
Iwu, M. M. "Root alkaloids of *Rauwolfia vomitoria* Afz." Planta medica 32.05 (1977): 88-94.*

* cited by examiner

*Primary Examiner* — John M Mauro
(74) *Attorney, Agent, or Firm* — Ladas & Parry LLP

(57) ABSTRACT

Present invention discloses a novel, commercially viable process for extraction of Alpha yohimbine from the bark, stem and leaves of *Rauwolfia* species. The extract is obtained by a precipitation method involving alternate steps of acidification and alkalization along with use of specific organic solvents. The extract gives higher yield of 7-8 fold as compared to other processes and without use of any column chromatography at all. Yield of alpha yohimbine from roots and leaves of *Rauwolfia canescens* by process of present invention was 0.017% and 0.4% respectively, indicating that leaves are a much better source. The HPLC analysis of the compound obtained indicated a purity of >90%.

12 Claims, 3 Drawing Sheets

PROCESS FOR EXTRACTING ALPHA YOHIMBINE (RAUWOLSCINE) FROM *RAUWOLFIA* SPECIES

CROSS REFERENCE TO RELATED APPLICATION

This application is a continuation of International Application No. PCT/IN2017/050518 filed on 09 Nov. 2017, which claims priority from Indian Application No. 201611038337 filed on 09 Nov. 2016, the contents of which should be understood to be incorporated herein by reference.

The present invention relates to natural extracts/herbal extracts. More specifically, it pertains to a novel process for the extraction of alpha yohimbine (rauwolscine) from *Rauwolfia* species. The process gives alpha yohimbine in significantly higher quantity and purity as compared to prior art methods.

BACKGROUND OF THE INVENTION

Terms and Definitions

Alkaloids—These are a group of naturally occurring chemical compounds that mostly contain basic nitrogen atoms (https://en.wikipedia.org/wiki/Alkaloid). They are of plant origin and have pronounced physiological actions on humans. They include many drugs (morphine, quinine) and poisons (atropine, strychnine).

Phytochemicals—These are compounds derived from plants.

Organic solvents—Organic solvents are a chemical class of compounds that share a common structure (at least 1 carbon atom and 1 hydrogen atom), low molecular weight, lipophilicity, and volatility, and they exist in liquid form at room temperature. They may be grouped further into aliphatic-chain compounds, such as n-hexane, and as aromatic compounds with a 6-carbon ring, such as benzene or xylene. Aliphatics and aromatics may contain a substituted halogen element and may be referred to as halogenated hydrocarbons, such as perchloroethylene (PCE or PER), trichloroethylene (TCE), and carbon tetrachloride. Alcohols, ketones, glycols, esters, ethers, aldehydes, and pyridines are substitutions for a hydrogen group. Organic solvents are useful because they can dissolve oils, fats, resins, rubber, and plastics. They are widely used in industry and in context of present invention, in the extraction of plant compounds (Ref: http://emedicine.medscape.com/article/1174981-overview).

Polar and Non-polar solvents: Organic solvents can be grouped into two categories—polar and non-polar. Polar solvents have large dipole moments (also known as "partial charges"); they contain bonds between atoms with very different electronegativities, such as oxygen and hydrogen. Non polar solvents contain bonds between atoms with similar electronegativities, such as carbon and hydrogen. Examples of some common polar and non-polar solvents (and their polarity values/dielectric constants) are: Polar—Ethyl acetate (5.3), Acetone (10.4), Water (16.0) and Acetonitrile (18.0) and Non-polar—Hexane, Benzene (0.0), Toluene (1.4) and Chloroform (3.1). Generally, solvents with dielectric constants greater than about 5 are considered "polar" and those with dielectric constants less than 5 are considered "non-polar." (http://chem.libretexis.org/Core/Organic_Chemistry/Fundamentals/Intermolecular_Forces/Polar_Protic_and_Aprotic_Solvents)

*Rauwolfia* Plant and its Significance

*Rauwolfia* is a genus of evergreen trees and shrubs in the family, Apocynaceae. The genus is named in honour of its discoverer Leonhard Rauwolf, a renowned German physician, botanist and explorer. The genus is mainly found in tropical regions of Africa, Asia, Latin America, and various oceanic islands. The best known species of *Rauwolfia* is *Rauwolfia caffra*, the South African quinine tree. *Rauwolfia* has 74 accepted species (http:www.theplantlist.org/browse/A/Apocynaceae/Rauwolfia/). *Rauwolfia serpentina*, commonly known as Indian Snakeroot or "Sarpagandha", contains a number of compounds which act as medicines/drugs e.g. including yohimbine, ajmaline, aricine, corynanthine, rauwolscine, reserpine, reserpiline, serpentinine etc. Another species, *Rauwolfia canescens* also contains a number of important phytochemicals. Different species of *Rauwolfia* differ in nature and quantities of phytochemicals present in them. In fact a study has been reported in New England Journal of Medicine in which two species of *Rauwolfia* viz. *Rauwolfia serpentina* and *Rauwolfia canescens* were compared for their anti-hypertensive effects and reduced side effects. It was found that *Rauwolfia canescens* was superior to *Rauwolfia serpentina* in terms of improved therapeutic effects and reduced side-effects. (www.nejm.org/doi/full/10.1056/NEJM/95610042551404).

5 species of *Rauwolfia* are native to India. *R. tetraphylla* L. syn. (*Compend. Indian Med. Plants*, Vol. I, Rastogi & Mehrotra, PID, New Delhi, 1990, p. 340) is an economically important plant, which is cultivated on commercial scale in India. The plant is important because of the presence of nearly 30 alkaloids in its roots: ajmalicine, reserpine, sapagine, deserpidine, rescinnamine, serpentine, ajmalidine, alloyohimbine, chandrine, corynathine, iscajmaline, neo ajmaline, papaverine, raunatine, raunoline, rauwolscine or (α-yohimbine), reserpiline, reserpinine, reserpoxidine, serpinine, serpentinine, thambine, ajmaline and yohimbine [(Farooqi and Sreeramu, 2001, *Cultivation of Medicinal and Aromatic Crops*. University Press Ltd., India, pp: 210-211), J. Amer. Chem. Soc. 79(5): 1217-1222].

INTRODUCTION TO THE PRESENT INVENTION

The present invention discloses a novel process for obtaining a specific compound—alpha yohimbine in high yields from *Rauwolfia* species, particularly leaves of *Rauwolfia canescens*. However, the process is neither material nor species restricting. It is equally applicable to extraction of alpha yohimbine from bark, stem, roots etc. and from any species of *Rauwolfia*, being a general chemical process for specific extraction of alpha yohimbine in high quantities and in highly purified form. However, the yield will vary from species to species depending upon amount of alpha yohimbine present in appropriate part of each species e.g. leaves, bark, stem, roots etc.

Yohimbine Vs Alpha-Yohimbine (Ranwolscine)

Yohimbine is an indole alkaloid extracted from the bark of the *Pausinystalia yohimbe* tree. Yohimbine hydrochloride is a standardized form of yohimbine that is available as a prescription drug in the United States. Yohimbe bark extract, generally contains low concentrations of yohimbine (6% indole alkaloids, of which only 10-15% is yohimbine). Therefore it is unknown if commercial preparations share the same effects of yohimbine hydrochloride. α-yohimbine (17α-hydroxy-20α-yohimban-16β-carboxylic acid methyl ester) or rauwolscine is one of the 3 diastereoisomers of yohimbine (17α-hydroxy-20β-yohimban-16α-carboxylic acid methyl ester) and does not possess side effects; the other two isomers are corynanthine and 3-epi-alpha-yohimbine. Alpha-Yohimbine has the same molecular formula and weight as yohimbine but owing to differences in the spatial arrangement of atoms, its properties are different. Yohimbine and Alpha-Yohimbine share the same molecular formula viz. $C_{21}H_{26}N_2O_3$ and Molecular Weight 354.44 g/mol. Structure of Yohimbine is given in FIG. 1 and that of Alpha-Yohimbine (Rauwolscine) in FIG. 2.

Clinical Importance of Alpha Yohimbine

In the present scenario where most of the population is heading towards junk/fast food which leads to several diseases and health issues. One of the serious health issue related to present time life style is obesity or fat. Many people try to opt for techniques for fast weight loss which is wrong in many aspects. There is need to develop natural sources which are reliable and effective without any side effect. Alpha yohimbine is one such compound which can effectively treat the excess of fat and help to burn in a short term fasting. Alpha yohimbine basically affects by increasing adrenaline levels in the body and inhibits the regulation of fat cells thereby resisting their growth and simultaneously burning fat.

The usefulness of alpha yohimbine for therapeutic purposes has been extensively reviewed, as below:
1. MacDonald et al (1988)—*Therapeutic applications of drugs acting on alpha-adrenoceptors; Department of Pharmacology & Toxicology*, University of Kuopio, Finland. Annals of Clinical Research [1988, 20(5):298-310]
2. Steven M Southwick et al (1999)—*Yohimbine use in a natural setting: effects on post-traumatic stress disorder; Biological Psychiatry* Aug. 1, 1999 Volume 46, Issue 3, Pages 442-444 DOI: http://dx.doi.org/10.1016/S0006-3223(99)00107-9
3. Z. P. Khan et al (2002)—*Alpha-2 and imidazoline receptor agonists—Their pharmacology and therapeutic role.* 6 Apr. 2002DOI: 10.1046/j.1365-2044.1999.00659.xBlackwell Science Lid.
4. Leila Moezi et al (2014)—*The role of alpha-2 adrenoceptors in the anticonvulsant effects of adenosine on pentylenetetrazole-induced seizure threshold in mice; Pharmacology Biochemistry and Behavior* Volume 126, November 2014, Pages 36-42; doi: 10.1016/j.pbb.2014.09.008.

Superior Therapeutic Profile of Alpha-Yohimbine as Compared to Yohimbine—

Alpha yohimbine (Rauwolscine) is more highly focused on alpha-2 receptors than alpha-1 receptors, as much as 50 times more than standard yohimbine! Since the alpha-2 receptors are in charge of fat storage and the alpha-1 receptors have a role in adrenaline production, this change in focus equals more targeted Yohimbe fat loss with less stimulant effects. There are differences in the way alpha yohimbine works on alpha-2 receptors as well. It is more specific for alpha-2b and alpha-2c receptors than for alpha-2a receptors due to which in addition to stimulating weight loss, alpha yohimbine increases motivation and focus and provides an energy boost, all with little or no yohimbine side-effects. Effect of alpha yohimbine on mood is similar to yohimbine but alpha yohimbine is slightly more potent.

Commercial Production of Alpha Yohimbine—Challenges
    i. Very low yield—not commercially viable
    ii. Low purity—compound obtained is contaminated with impurities which spoils commercial value
    iii. Raw material source is non-renewable viz. BARK.

A number of methods have been disclosed in the prior art relating to extraction and quantitation of indole alkaloids including alpha yohimbine but all suffer from the limitations of low yield. The methods are more suited to laboratory scale purification of small quantities of compounds for research purposes than large scale purification at commercial level in an economically viable manner.

Some of the Prior Art Methods are Discussed Below:

US Patent Application No. 20120184576 A1 (U.S. Pat. No. 9,018,226 B2) entitled "Antipsychotic agents and standardized antipsychotic fractions from *Rauwolfia tetraphylla* and process of their isolation" discloses extraction of alkaloids, including alpha yohimbine from the leaves of *Rauwolfia tetraphylla*. The methodology is complex involving multiple fractionation techniques involving use of organic solvents, acidification and basification and also use of column chromatography (flash chromatography) to fractionate alpha yohimbine from other compounds. The method is more of a laboratory scale method for isolation and purification of alkaloid compounds from *Rauwolfia* sp. for research purposes, than a process for commercial scale production of alpha yohimbine.

The process of present invention differs from the prior art process in two main aspects viz. absence of column chromatography and higher yield.
    i. Column chromatography/flash chromatography not used at all: Unlike the prior art process which uses 'flash chromatography' to obtain alpha yohimbine from the alcohol or chloroform extracts of the leaves of *Rauwolfia tetraphylla*, the process of present invention does not use column chromatography at all. This results in technical benefits of reduced extraction cost (since cost of matrix of column is eliminated), faster extraction (column extraction slows the extraction process) and also higher yields. (Note: Flash chromatography is a modified form of preparative column chromatography which differs from the conventional technique in two ways: first, slightly smaller silica gel particles (250-400 mesh) are used, and second, due to restricted flow of solvent caused by the small gel particles, pressurized gas (ca. 10-15 psi) is used to drive the solvent through the column of stationary phase. (www.https://yvesrubin.files.wordpress.com/2011/03/flash_chromatography.pdf)
    ii. Higher Yields: The process of present invention, even without use of column chromatography results in substantially higher yields and higher purity of alpha yohimbine. The yield of alpha yohimbine obtained in prior art process (U.S. Pat. No. 9,018,226 B2) in Methanolic fraction is 29.1 mg yield from 100 gram leaves (190 grams of leaves yield 15 mg in one fraction and 40.3 mg in another fraction i.e. total yield of 15 mg+40.3 mg i.e. 55.3 mg from 190 grams of leaves or 29.1 mg from 100 gram leaves); and in Chloroform fraction the yield is 63 mg yield from 100 gram leaves: 190 grams of leaves yield 120 mg of alpha yohimbine. In contrast, the yield of alpha yohimbine by process of present invention is 400 mg per 100 gram leaves i.e. approximately 7-8 fold! Comparison of the prior art method with process of present invention is given in Table 1 below:

TABLE 1

Comparison of extraction process of present invention with a prior art process for extraction of alpha yohimbine from *Rauwolfia* sp. leaves

| S. No. | Process of Prior Art (US 20120184576 A1) | Process of Present Invention |
|---|---|---|
| 1. | Extraction and purification<br>Two step.<br>Extraction and purification carried out separately. Extraction carried out by use of specific solvents and purification is carried out by using column chromatography (flash chromatography). | Single step.<br>Extraction and purification of alpha yohimbine is carried out in a single step, without use of column chromatography and by use of specific solvents combined with alternate steps of acidification and alkalization to obtain desired compound in high quantity and of high purity. |
| 2. | Yield<br>Low.<br>63 mg/100 g dry leaves | High (7-8 times)<br>400 mg/100 g dry leaves |
| 3. | Commercial viability<br>No<br>Yield is too less for process to be commercially viable. Suitable for laboratory scale production/research work etc. where very less quantities of compounds are needed. | Yes<br>Yield is high. Process is simple involving use of organic solvents only and easily scalable. No special equipment e.g. special columns etc. needed at all. |

Extraction and Purification of Alpha Yohimbine Along With Other Alkaloids from Leaves of *Rauwolfia tetraphylla*

A number of workers have reported lab scale purification of alpha yohimbine along with other alkaloids from leaves of *Rauwolfia tetraphylla*. Various methods and analytical techniques reported in prior art are discussed below:

Gupta Shikha et al 2012 (*HPTLC method for the simultaneous determination of four indole alkaloids in Rauwolfia tetraphylla: A study of organic/green solvent and continuous/pulse sonication*) Journal of Pharmaceutical and Biomedical Analysis Volume 66, July 2012, Pages 33-39) have disclosed a new validated high-performance thin-layer chromatographic (HPTLC) method for the simultaneous quantitation of four antipsychotic indole alkaloids (IAs), reserpiline, α-yohimbine, isoreserpiline and 10-methoxy tetrahydroalstonine as markers in the leaves of *Rauwolfia tetraphylla*. The technique uses percolation, ultrasonication and microwave techniques. Non-ionic surfactants, viz. Triton X-100, Triton X-114 and Genapol X-80 were used for extraction and no back-extraction or liquid chromatographic steps were used to remove the targeted IAs from the surfactant-rich extractant phase.

Verma Ram Kishore et al 2012—(A simple isocratic HPLC method for the simultaneous determination of antipsychotic indole alkaloids in *Rauwolfia tetraphylla*) Journal of Liquid Chromatography & Related Technologies Volume 35, Issue 7, 2012) disclose simple isocratic HPLC method for the simultaneous quantitation of three antipsychotic indole alkaloid (IA), α-yohimbine, iso-reserpiline, and 10-methoxy tetrahydroalstonine in *Rauwolfia tetraphylla* leaf. Samples were analyzed by reverse-phase chromatography on a waters spherisorb column using isocratic elution with acetonitrile containing 0.1% TEA and water containing 0.1% TFA (35:65, v/v) at a flow rate of 1 mL/min, a column temperature of 30° C., and UV detection at 210 nm. The method was validated and applied for quantification of individual alkaloids in various leaf extracts of *R. tetraphylla*.

Kumar et al 2011 (*Quantitative determination of Yohimbine alkaloid in the different part of the Rauwolfia tetraphylla*) Journal of Chemical and Pharmaceutical Research J. Chem. Pharm. Res., 2011, 3(2):907-910} discloses the use of methanolic extract of leaves, stem and roots of *Rauwolfia tetraphylla* and yohimbine to quantitatively determine the amount of yohimbine in different parts of the plant.

These disadvantages have been overcome in the present invention which discloses an improved process for commercial level production of alpha yohimbine.

The improved process of the present invention offers the following advantages:

i. High yield—up to 400 mg per 100 grams of leaves or 0.4%
ii. High purity-90 to 93%
iii. Low-cost, fast and economical process which does not require any columns or sophisticated equipment Innovative Approach Used in the Process of Present Invention Prior art methods have used column chromatography and expensive matrices to purify alpha-yohimbine. Column chromatography reduces yields and enhances the cost of extraction, making it unviable for extraction and purification of compounds at commercial scale, though it is very much suitable for laboratory scale preparation. IN NOVEL PROCESS OF THE PRESENT INVENTION, COLUMN CHROMATOGRAPHY IS NOT USED AT ALL BUT STILL HIGHLY PURIFIED COMPOUND IS OBTAINED IN HIGH YIELD AT COMMERCIAL LEVEL. This has been achieved by an innovative approach of using a sequence of steps involving use of specific, water-immiscible organic solvents and change of pH of water to extract and purify the desired compound of interest i.e. alpha-yohimbine to high purity i.e. 90-93% and also obtain it in high yields. Yield by present process is 7-8 times as compared to a prior art method (US 20120184576A1) which used the same raw material i.e. *Rauwolfia canescens*.

OBJECTS OF THE PRESENT INVENTION

The primary object of the present invention is to disclose an improved and commercially viable process for extraction of Alpha-Yohimbine in which the yield and purity is significantly higher than prior art processes.

One more object of the present invention is to disclose use of renewable source i.e. leaves of a specific species of *Rauwolfia* i.e. *Rauwolfia canescens*, as a raw material instead of bark, because it contains higher % of the active compound, resulting in higher yield.

Another object of the present invention is to disclose a process for obtaining high purity (upto 95%) alpha yohimbine from the leaves of *Rauwolfia* species i.e. *canescens*.

SUMMARY OF THE INVENTION

Present invention discloses a novel, commercially viable process for extraction of Alpha yohimbine from the bark, stem and leaves of *Rauwolfia* species. The extract is obtained by a precipitation method involving alternate steps of acidification and alkalization along with use of specific organic solvents. The extract gives higher yield of 7-8 fold as compared to other processes and without use of any column chromatography at all. Yield of alpha yohimbine obtained from roots and leaves of *Rauwolfia canescens* by process of present invention was 0.017% and 0.4% respectively, indicating that leaves are a much better source. The purity of the compound obtained as determined by HPLC analysis was 90-93%.

DETAILED DESCRIPTION OF THE INVENTION

Figure 1:
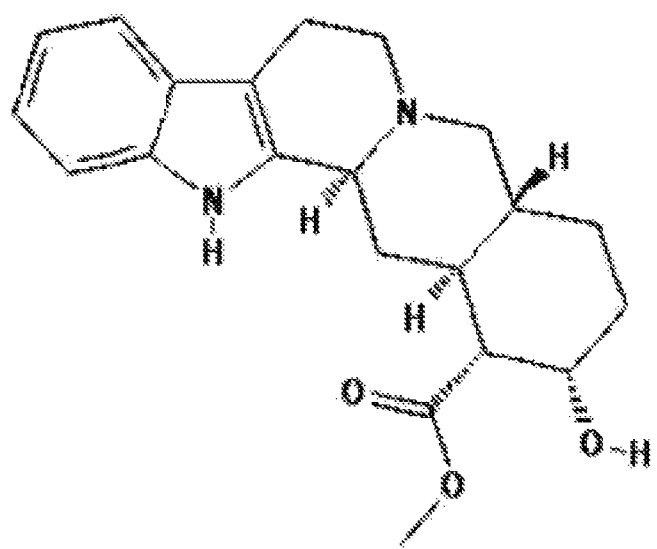
FIG. 1: Structure of Yohimbine.
Figure 2:
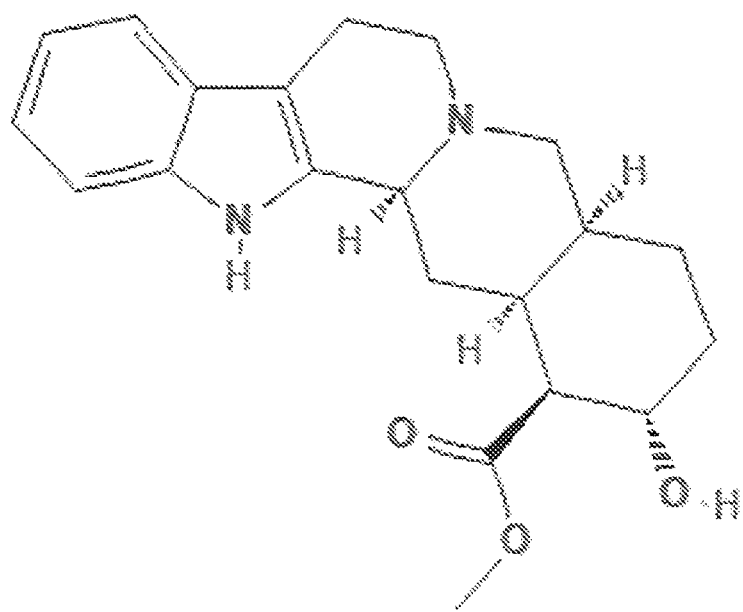
FIG. 2: Structure of Alpha-Yohimbine (Rauwolscine).
Figure 3:
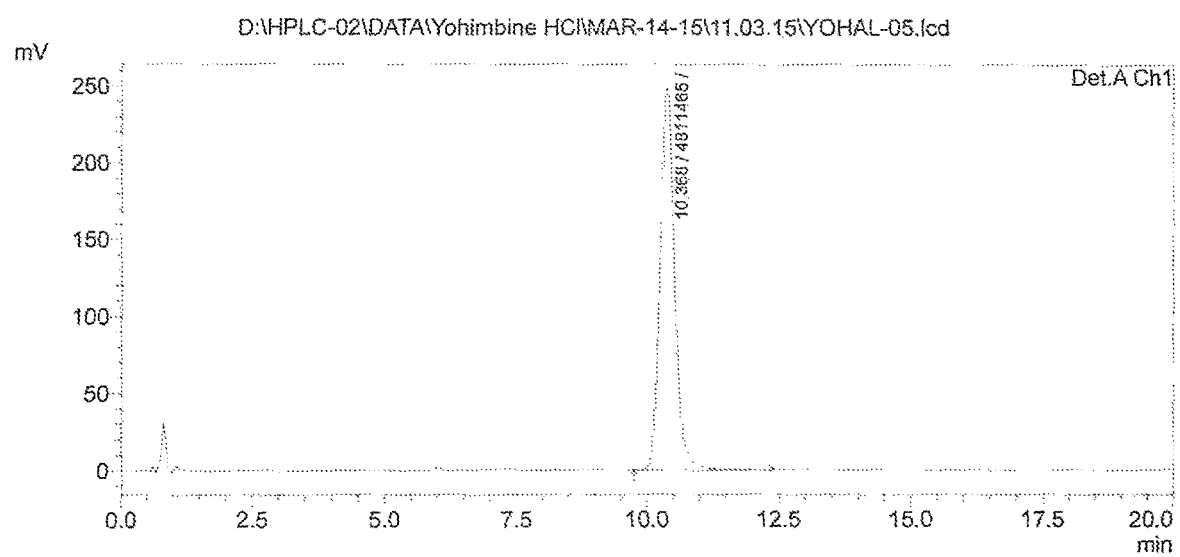
FIG. 3: HPLC analysis to determine the purity.

Present invention discloses a novel, commercially viable process for extraction of Alpha yohimbine from the leaves of *Rauwolfia* species though bark and stem can also be used. The advantage of using leaves is that it represents a renewable source which is easily available and easy to handle and process. Secondly, the improved process of present invention increases the yield of alpha yohimbine by 7-8 fold which is quite remarkable. Unlike prior art methods which suffer from the limitations of very poor yield and low purity of the compound obtained, the method of present invention yields the desired compound i.e. Alpha yohimbine in high quantities (upto 7-8 fold increase over existing methods) and in high purity (95% vs 39% in a prior art method using leaves of *Rauwolfia* species. Comparison of extraction process of alpha yohimbine from leaves of *Rauwolfia* species with a prior art process (US 20120184576 A1) is given in Table 1 above.

Challenges in Extraction of Pure Molecules from Plant Material—

Extraction of desired molecules from plant sources poses several challenges, especially low yields and low impurities. The extract from plant material e.g. root, stem, leaf, bark, fruit, flower, seeds or whole plant is often contaminated with undesirable impurities which lower the commercial value of the product besides posing health risks due to presence of undesirable impurities. Hence, it is highly desirable to develop suitable processes/methods to obtain desired molecules of high purity and in high quantity.

Existing Approaches for Obtaining Desired Molecules from Plant Products and their Limitations—

Plants are a rich source of various chemicals and compounds. These are commonly referred to as "Phytochemicals" i.e. chemicals derived from plants. Depending upon the nature of atoms present and also types of chemical groups present in the compounds/molecules, the molecules differ in size and polarity. These differences in size and polarity form the basis of various separation techniques e.g. chromatography, solvent extraction and also acidification/alkalization which are commonly used at commercial level to extract desired molecules from plants.

Limitations—

Gel permeation and ion-exchange chromatography exploit differences of size and charge of the molecules respectively to bring about separation and purification of the molecules. However, they suffer from the limitation of being extremely slow, cumbersome and also use of expensive matrices (packing material inside the column). The yield is also quite low though purity of the desired molecules may be high. Solvent extraction offers the benefit of low-cost, high yield but suffers from the limitation of low purity of the molecules obtained.

From the above it is clear that no process is available in the prior art for production of alpha yohimbine at commercial scale and high purity level. Both these challenges viz. commercial/industrial scale production and high level of purity of alpha yohimbine have been overcome by the process of present invention which is simple, economical and results in high yields of alpha yohimbine with high purity levels of between 90-96%.

Theoretical Concepts Involved in Process of Present Invention

To ensure better understanding of the process of the invention, the theoretical aspects involved are discussed. It is a known fact in chemistry that 'like dissolves like' i.e. a solvent which is polar will dissolve a compound which is polar and not a compound which is non-polar e.g. water is polar and oil is non polar. Hence, water will not dissolve oil since nature of both are entirely different i.e. polar and non-polar will not mix. Plants contain a number of compounds and depending upon their composition of atoms and arrangement of groups, the compounds may be polar, non-polar, strongly polar/weakly polar etc. Hence, when extraction is carried out with non-polar and polar solvents, depending upon their polarity, the compounds get 'extracted' into the appropriate phase e.g. highly polar compounds get extracted with water, while non-polar are not extracted. The polarity of a solvent or a compound depends upon the number of polar groups present in it. Polar value of some of the commonly used solvents for preparation of plant extracts is given in Table 2 below:

TABLE 2

Polarity of some commonly used solvents in plant extracts

| S. No. | Non-Polar Solvent | Polar Value | Polar Solvent | Polar Value |
|---|---|---|---|---|
| 1. | Hexane, Benzene | 0.0 | Ethyl acetate | 5.3 |
| 2. | Toluene | 1.4 | Dichloromethane | 7.3 |
| 3. | Diethyl ether | 2.9 | Acetone | 10.4 |
| 4. | Chloroform | 3.1 | Acetonitrile | 18.0 |
| 5. | 1,4-Dioxane | 1.8 | Water | 16.0 |

Data Source: https://en.wikipedia.org/wiki/Solvent

When a solvent or a mixture of solvents is added to a plant material, it will 'draw out' the chemical compounds which are of 'like' or 'similar' nature i.e. polar solvents will extract polar compounds and non-polar compounds will be extracted by non-polar solvents. Solvents of similar polarity to that of the compounds being extracted will be more suitable than those whose polarity is different.

Thus one can extract different compounds at different steps of extraction by using a particular solvent or a mixture of solvents. However, loss of some quantity of the desired compound invariably occurs when number of extraction steps is more, leading to low yields. However, more steps of extraction with different solvents result in high purity compounds. When number of steps of extraction are reduced, yield increases but purity decreases.

One way to overcome this problem is to separate the extraction and purification steps. Extraction is carried out using organic solvents which gives good yields but desired compound is of low purity. However, if high purity compound is required, then purification is carried out using suitable chromatographic techniques e.g. column chromatography.

Extraction of Compounds Using Organic Solvents Along with Acidification/Alkalization Apart from 'polarity', another factor affecting solubility of plant compounds and hence 'extraction' is pH i.e. the acidic or basic nature of the solvent. By addition of an acid or a base to an organic solvent, its properties can be drastically altered and separation of compounds can be achieved. The concept is further elaborated below:

Compounds (Salts), which are ionic, tend to be water-soluble while neutral molecules tend not to be. The addition of an acid to a mixture of an organic base and acid will result in the acid remaining uncharged, while the base will be protonated to form a salt. If the organic acid, such as a carboxylic acid, is sufficiently strong, its self-ionization can be suppressed by the added acid. Conversely, the addition of a base to a mixture of an organic acid and base will result in the base remaining uncharged, while the acid is deprotonated to give the corresponding salt. Once again, the self-ionization of a strong base is suppressed by the added base. The acid-base extraction procedure can also be used to separate very weak acids from stronger acids and very weak bases from stronger bases, as long as the difference of their pKa (or pKb) constants is large enough e.g. weak acids with phenolic OH groups like phenol, 2-naphthol, or 4-hydroxyindole (pKa around 10) from stronger acids like benzoic acid or sorbic acid (pKa around 4-5); very weak bases like caffeine or 4-nitroaniline (pKb around 13-14) from stronger bases like mescaline or dimethyltryptamine (pKb around 3-4).

Usually the pH is adjusted to a value roughly between the pKa (or pKb) constants of the compounds to be separated. Weak acids like citric acid, phosphoric acid, or diluted sulfuric acid are used for moderately acidic pH values, and hydrochloric acid or more concentrated sulfuric acid is used for strongly acidic pH values. Similarly, weak bases like ammonia or sodium bicarbonate ($NaHCO_3$) are used for moderately basic pH values while stronger bases like potassium carbonate ($K_2CO_3$) or sodium hydroxide (NaOH) are used for strongly alkaline conditions. In present case, the pKa value of the target compound i.e. alpha yohimbine is 6.34. Optimization of various solvents and acidification steps was carried out by inventors resulting in a novel process which gave high yields and desired purity of alpha yohimbine.

Methodology

The process comprises of the following 7 steps:
1. Organic solvent-Alkaline extraction step: Appropriate part of *Rauwolfia* sp. viz. bark, stem, root etc. in dried and powdered form is extracted multiple times, optimally 3 times, with a water-immiscible, non-polar organic solvent preferably toluene, at 40-50° C. in ratio of 1:4 i.e. 1 part solid and 4 parts solvent and made alkaline (pH 9-9.5) by addition of alkali, preferably 20-25% solution of ammonia and keeping for 4 hours in reactor with stirring followed by filtration. The filtrates/extracts are then pooled.
2. Organic solvent-Acidic extraction step: The pooled organic solvent extracts are then made acidic (pH 3.5±0.5) by addition of acid solution, preferably tartaric acid and extracted multiple times, optimally 3 times, with purified water in optimal ratio of 12:1 v/v (volume of pooled fraction: volume of water), to extract alpha yohimbine (rauwolscine) into acidified aqueous layer with high efficiency.
3. Alkalinisation of aqueous layer: The acidified aqueous layer containing alpha yohimbine (rauwolscine) is then made alkaline (pH 9.0-9.5) and extracted multiple times, optimally 3 times with chlorinated, non-polar solvent such as chloroform (4:1 v/v; volume of aqueous pooled fraction: volume of solvent) to extract alpha yohimbine (rauwolscine) into the organic layer and leave impurities behind in the basic aqueous layer.
4. Recovery of alpha yohimbine from organic solvent by evaporation of solvent: Alpha yohimbine (rauwolscine) is obtained as dry residue from the organic layer by distillation to evaporate the solvent.
5. Conversion of extracted compound to salt: The dry residue is then dissolved in ethyl acetate (4-5 times the weight of residue) and pH lowered to acidic (3-3.5) by addition of acid, preferably oxalic acid to precipitate Alpha yohimbine (rauwolscine) as salt and recover the same by filtration followed by drying at 60-70 degree C. for 1-2 hours.
6. Removal of impurities from extract by washing with water and change of pH: The cooled and dried extract of alpha yohimbine (rauwolscine) is purified further by dissolving in water (5 times the dry weight) followed by addition of alkali to raise pH to 9-9.5 to precipitate the compound and recover the same by filtration followed by drying at 60-70 degree C. for 1-2 hours.
7. Final purification step: The partially purified alpha yohimbine (rauwolscine) compound is dissolved in polar organic solvent such as ethanol, methanol, acetone, ethyl acetate etc. (10 times the weight of residue). The solution is treated with charcoal to remove colour impurities. The clear solution obtained is acidified to pH 2.0-2.5 using acid, preferably hydrochloric acid and cooled to 15-20 degree C. to give maximum precipitation or yield of highly pure (>90%) alpha yohimbine hydrochloride which is filtered and dried to obtain the final product in form of white/off-white fine powder of Alpha Yohimbine Hydrochloride.

The following example is of the best-contemplated mode of carrying out the invention. The description is made for the purpose of illustrating the general principles of the invention and should not be taken in a limiting sense.

Example

Collection of raw material and powdering: 1000 g leaves of *Rauwolfia canescens* were collected, dried in the sun and powdered. Extraction was then carried as described in the steps below:

1. Organic solvent—Alkaline extraction step: The powder was then mixed with water immiscible solvent viz. any non-polar organic solvent such as toluene etc. preferably toluene at 40-50° C. in ratio of 1:4 i.e. 1 part solid and 4 parts solvent and made alkaline by addition of 20-25% ammonia solution, pH 9-9.5 (alkaline) and kept for 4 hours in reactor with stirring followed by filtration. The filtrates/extracts were then transferred to another vessel. The remaining solid material was extracted twice with same solvent as above and the filtrates were pooled in the same vessel.

2. Organic solvent-Acidic extraction step: The pooled fractions were then made acidic by addition of tartaric acid solution (pH 3.5±0.5) and extracted with purified water in optimal ratio of 12:1 v/v (volume of pooled fraction: volume of water). As a result the impurities were left behind in the organic layer and the compound of interest was transferred to the acidified aqueous layer. This step was also performed twice, resulting in high extraction efficiency.

3. Alkalization of aqueous layer: The aqueous layer containing compound of interest was then basified with 20-25% ammonia solution to pH 9.0-9.5 and extracted with chlorinated solvent such as methylene dichloride, chloroform etc. preferably chloroform, (4:1 v/v; volume of aqueous pooled fraction: volume of solvent) due to which compound of interest was extracted into the organic layer and impurities remained behind in the basic aqueous layer.

4. Recovery of aloha yohimbine from organic solvent by evaporation of solvent: Alpha yohimbine (rauwolscine) was obtained as dry residue from the organic layer by distillation to evaporate the solvent.

5. Conversion of extracted compound to salt: To the dry residue remaining behind, ethyl acetate was added (4-5 times the weight of residue) to dissolve the material containing compound of interest completely. Then pH was again lowered to acidic by addition of acid, preferably oxalic acid, due to which the desired compound was converted to salt form and precipitated out. The precipitate was collected by filtration using filter cloth and precipitate was dried by heating to 60-70 degree C. for 1-2 hours.

6. Removal of impurities from extract by washing with water and change of pH: The dried extract was cooled to room temperature and dissolved in water. The compound was precipitated out by making the solution alkaline (pH 9-9.5) by addition of 20-25% ammonia solution while the impurities were left behind in water. Precipitate was recovered by filtration and dried as before.

7. Final purification step: Dried material was dissolved in polar organic solvent such as ethanol, methanol, acetone, ethyl acetate etc. The solution was treated with charcoal to remove colour impurities. The clear solution obtained was acidified with HCl to pH 2.0-2.5 and cooled to 15-20 degree C. to give maximum precipitation or yield of Alpha Yohimbine Hydrochloride. The precipitate was filtered and dried to obtain the final product in form of white/off-white fine powder of Alpha Yohimbine hydrochloride.

The yield of the product obtained when using roots and leaves is given in Table 3 below.

TABLE 3

| \multicolumn{5}{c}{Yield of alpha yohimbine from roots and leaves of *Rauwolfia canescens*} |
| S. No. | Herb part | Batch Quantity | Yield | Yield % | Assay of alpha yohimbine (HPLC) |
| --- | --- | --- | --- | --- | --- |
| 1 | Root | 500 kg | 87 g | 0.0174% | 82% |
| 2 | Leaves | 500 kg | 2-2.5 kg | 0.4%-0.5% | 90-93% |

Novelty—

The novelty of the present invention lies in disclosing a simple, commercially viable process for extraction of alpha yohimbine from *Rauwolfia* species, in high quantities and with high purity (>90%), without use of column chromatography.

Inventive Step—

The technical advancement of knowledge lies in disclosing a commercially viable process for the extraction of alpha yohimbine from *Rauwolfia* species with the help of organic solvents and alternate steps of acidification and alkalization that provides greater yields and also much higher purity of the compound (>90%) as compared to other processes. The method also excludes the need of expensive and time consuming techniques such as column chromatography. The process has economic importance because it considerably reduces the cost of alpha yohimbine owing to higher yields, faster processing time and simplicity of the process.

INDUSTRIAL APPLICATION

Alpha yohimbine is used as an aphrodisiac, for impotence, erectile dysfunction, athletic performance, weight loss, exhaustion, angina, hypertension, diabetic neuropathy, and postural hypotension. Due to its varied application in the medicinal field the extraction process of alpha yohimbine has considerable industrial applications.

We claim:

1. A process for extraction of alpha yohimbine (rauwolscine) from *Rauwolfia* species wherein the process comprises the following steps:
    (i) organic solvent-alkaline extraction step:
        (ia) providing *Rauwolfia* sp. plant matter selected from bark, stem, root and mixtures thereof, in dried and powdered form;
        (ib) mixing the plant matter with a water-immiscible, a non-polar organic solvent and a basic solution, wherein the basic solution is present in a quantity sufficient to render the alpha yohimbine soluble in the water-immiscible, non-polar organic solvent, wherein the ratio of solid plant matter: organic solvent is 1:4 (w/v), wherein the basic solution has a pH of 9-9.5;
        (ic) stirring the mixture at 40-50° C. for 4 hours to extract alpha yohimbine into the organic solvent;
        (id) filtering the stirred and heated mixture to obtain a first basic organic solvent filtrate containing extracted alpha yohimbine and a first solid residue at least partially depleted in alpha yohimbine;
        (ie) mixing the first solid residue at least partially depleted in alpha yohimbine with the water-immiscible, non-polar organic solvent and the basic solution, wherein the ratio of solid residue: solvent is 1:4 (w/v);

(if) repeating steps (1c)-1(e) one or more times to obtain one or more subsequent basic organic solvent filtrate extracts containing yohimbine and one or more subsequent solid residues at least partially depleted in alpha yohimbine;

(ig) combining the first basic solvent organic extract and the one or more subsequent basic solvent organic extract(s) containing alpha yohimbine to obtain a pooled basic solvent organic extract containing alpha yohimbine;

(ii) organic solvent-acidic extraction step:

(iia) acidifying the pooled basic solvent organic extract containing alpha yohimbine by addition of an amount of an acid solution sufficient to render the alpha yohimbine soluble in water;

(iib) extracting the acidified extract with purified water in a ratio of 12:1 (v/v) volume of pooled extract: volume water to obtain a first acidified aqueous extract containing alpha yohimbine and a liquid organic extract at least partially depleted in alpha yohimbine;

(iic) repeating the extraction of the acidified organic extract at least partially depleted in alpha yohimbine with purified water in a ratio of 12:1 (v/v) one or more times to obtain one or more subsequent acidified aqueous extract(s) containing alpha yohimbine;

(iie) combining the first and subsequent acidified aqueous extract(s) to obtain a pooled acidic aqueous extract containing alpha yohimbine;

(iii) alkalinisation of aqueous acid extract step:

(iiia) rendering the pooled acidic aqueous extract containing alpha yohimbine alkaline by addition of a base, wherein the pH of the alkalinized aqueous extract is 9.0-9.5;

(iiib) extracting the alkalinized aqueous extract with a chlorinated-solvent in a ratio of 4:1 (v/v) volume of alkalinized extract: volume of chlorinated-solvent to obtain a first basic chlorinated-solvent extract containing alpha yohimbine and a basic aqueous extract comprising impurities;

(iiic) repeating extraction of the basic aqueous extract with chlorinated-solvent one or more times to obtain one or more subsequent basic chlorinated-solvent extract(s) containing alpha yohimbine and one or more subsequent basic aqueous extract(s) comprising impurities;

(iiid) combining the first basic chlorinated-solvent extract containing alpha yohimbine and the subsequent basic chlorinated-solvent extract(s) containing alpha yohimbine to obtain a pooled basic chlorinated-solvent extract containing alpha yohimbine;

(iv) recovery of alpha yohimbine from organic liquid extract step:

(iva) subjecting the pooled basic chlorinated-solvent extract containing alpha yohimbine to distillation of the chlorinated-solvent;

(ivb) obtaining alpha yohimbine contained therein as a dry residue;

(v) conversion of extracted alpha yohimbine to a salt step:

(va) dissolving the dried and cooled residue containing alpha yohimbine in ethyl acetate in a ratio of 4-5:1 (w/w) ethyl acetate: residue.

(vb) acidifying the resulting solution to a pH of 3-3.5 by addition of acid;

(vc) recovering precipitated alpha-yohimbine salt by filtration (vd) drying said alpha-yohimbine salt at 60-70° C. for 1 to 2 hours;

(vi) additional removal of impurities step:

(via) dissolving the dried and cooled residue containing alpha yohimbine salt in water at a ratio of 5:1 water: dried extract (w/w);

(vib) adding a base to the solution to raise the pH to 9-9.5

(vic) recovering precipitated partially purified alpha yohimbine by filtration;

(vid) drying the recovered partially purified alpha yohimbine at 60-70° C. for 1 to 2 hours;

(vii) final purification step:

(viia) dissolving the dried partially purified alpha yohimbine in a polar organic solvent in a ratio of 10:1 of solvent: dried partially purified alpha yohimbine (w/w);

(viib) treating the solution with charcoal to remove colored impurities;

(viic) acidifying the treated solution and cooling the acidified solution to 15 to 20° C. to effect precipitation of solid alpha yohimbine hydrochloride;

(viid) filtering the acidified and cooled mixture so-obtained and drying the solid precipitate to obtain alpha yohimbine hydrochloride as a fine powder.

2. The process of claim 1, wherein the base used to make the solution alkaline in steps (i), (iii) and (vi) is a 20-25% ammonia solution.

3. The process of claim 1, wherein the acid used to make the solution acidic in step (ii) is tartaric acid.

4. The process of claim 1, wherein the acid used to make the solution acidic in step (v) is oxalic acid.

5. The process of claim 1, wherein the acid used to make the solution acidic in step (vii) is hydrochloric acid.

6. The process of claim 1, wherein the chlorinated-solvent used for extraction of the alkalinized aqueous extract containing alpha yohimbine in step (iii) is chloroform.

7. The process of claim 1, wherein in step (if) the extraction with the water-immiscible non-polar organic solvent is carried out two times.

8. The process of claim 1, wherein step (iic) is carried out two times.

9. The process of claim 1, wherein step (iiic) is carried out two times.

10. The process of claim 1, wherein in step (viia) the polar organic solvent is selected from the group consisting of ethanol, methanol, acetone, ethyl acetate and mixtures thereof.

11. The process of claim 1, wherein in steps (ib)-(if) the non-polar organic solvent is toluene.

12. The process of claim 1, wherein the extraction of the plant matter or the residue partially depleted in alpha yohimbine in steps (ib)-(if) is carried out a total of three times.

* * * * *